United States Patent
Marini

(12) 
(10) Patent No.: US 6,328,987 B1
(45) Date of Patent: Dec. 11, 2001

(54) COSMETIC SKIN CARE COMPOSITIONS CONTAINING ALPHA INTERFERON

(75) Inventor: Jan L. Marini, San Jose, CA (US)

(73) Assignee: Jan Marini Skin Research, Inc., San Jose, CA (US)

( * ) Notice: Subject to any disclaimer, the term of this patent is extended or adjusted under 35 U.S.C. 154(b) by 0 days.

(21) Appl. No.: 09/705,319

(22) Filed: Nov. 3, 2000

(51) Int. Cl.[7] ............................... A61K 7/00; A61K 7/40; A61K 31/74; A61K 7/42

(52) U.S. Cl. ....................... 424/407; 424/78.03; 424/59

(58) Field of Search ........................ 424/401, 59, 78.03

(56) References Cited

U.S. PATENT DOCUMENTS 4,957,734 * 9/1990 Miller .................................. 424/85.7
5,686,489 * 11/1997 Yu et al. .............................. 514/557
5,853,755 12/1998 Foldvari .............................. 424/450

OTHER PUBLICATIONS

Foldvari et al. (1998) "Palmitoyl Derivatives of Interferon α: Potential for Cutaneous Delivery." *Journal of Pharmaceutical Sciences,* vol. 87(10):1203–8.

Foldvari et al. (1999) "Dermal and transdermal delivery of protein pharmaceuticals: lipid–based delivery systems for interferon α." *Biotechnol. Appl. Biochem.,* vol. 30:129–137.

* cited by examiner

*Primary Examiner*—Thurman K. Page
*Assistant Examiner*—Rachel M. Bennett
(74) *Attorney, Agent, or Firm*—Pamela J. Sherwood; Bozicevic, Field & Francis LLP

(57) ABSTRACT

Cosmetic skin care compositions containing alpha interferon are provided. The compositions improve the appearance of aged or damaged skin.

10 Claims, No Drawings

COSMETIC SKIN CARE COMPOSITIONS CONTAINING ALPHA INTERFERON

BACKGROUND OF THE INVENTION

Maintaining a youthful appearance is of great importance to many people, particularly in an aging population. Several of the visible signs of aging result from its effects on the skin. The passage of time is reflected in the appearance of wrinkles and fine lines; by a slackening of tissue; a loss of cutaneous elasticity; a leathery or dry appearance; and by the yellowing of the skin which becomes duller and loses its radiance. Skin that has been consistently exposed to sunlight throughout life, particularly the face and hands, may show pigmentation marks, telangiectasia and elastosis. At the histological level, skin damage from photoaging is shown in tangled, thickened, abnormal elastic fibers, decreased collagen and increased glycosaminoglycan content. The aging process also results in thinning and deterioration of the skin. There is a reduction in cells and in blood supply, and a flattening in the junction between the dermis and epidermis.

Treatments designed to prolong or promote youthful appearance include topical applications of cosmetic preparations, lotions and moisturizer, electrical stimulation, collagen injections and cosmetic surgery. However, there is still a serious need for skin care compositions that treat wrinkles and fine lines, and restore the youthful appearance of the skin.

Relevant Literature

The use of alpha interferon in antiviral topical creams is reviewed by Foldvari et al. (1999) *Biotechnol Appl Biochem* 30 (Pt 2):129–37. The creams utilize liposome encapsulated, and or fatty acid acylated derivatives in the formulations. For example, palmitoyl derivatives of interferon alpha2b (p-IFNalpha) were prepared by covalent attachment of the fatty acid to lysine residues in the protein through a reaction with N-hydroxysuccinimide palmitate ester (Foldvari et al. (1998) *J Pharm Sci* 87(10):1203–8). Descriptions of the liposome compositions may be in found in U.S. Pat. No. 5,853,755, issued Dec. 29, 1998.

SUMMARY OF THE INVENTION

The present invention features novel cosmetic skin care compositions for treating wrinkles and fine lines; firming skin tissue; and reviving the radiance of the skin. The skin care compositions comprise an alpha interferon and a cosmetically acceptable vechile.

This invention also features methods for the treatment of wrinkles and fine lines; firming skin tissue; and reviving the radiance of the skin, comprising topically applying thereto a cosmetic skin care composition containing an alpha interferon at a concentration of from about 0.5 to 500 U/ml.

DETAILED DESCRIPTION OF THE EMBODIMENTS

Topical compositions are provided for the treatment of wrinkles and fine lines; firming skin tissue; and reviving the radiance of the skin. The skin care compositions comprise an alpha interferon at a concentration of from about 0.5 to 500 U/ml, and a cosmetically acceptable vehicle. The alpha interferon in the composition is preferably free of liposomal encapsulation, and is preferably free of covalently bonded fatty acids not present in native forms of the protein. In a preferred embodiment, the interferon is the human alpha 2b subtype.

The compositions of the invention find use in improving the appearance of fine lines and wrinkles. The compositions may also be used in the treatment of irritated skin, e.g. minor rashes and burns. Further examples of minor skin irritations include acne, cold sores, dry skin, sunburn, cuts, insect bites, laser burns such as those resulting from cosmetic surgery, pruritic lesions and other inflammatory and non-inflammatory lesions of the skin.

Alpha Interferon

Human alpha interferons comprise a family of about 30 protein species, encoded by at least 14 different genes and about 16 alleles. Some of these alpha interferon protein species have been shown to have potent biological activities, including antiviral, antigrowth and immunoregulatory activity. Family members of particular interest include the alpha 2 interferons, e.g. IFN-α2a, IFN-α2b, IFN-α2c. Other alpha interferons that may find use in the present invention include α4a; α4b; α8a; α4a; α8c; α8b; α14c; α10a; α16; α1a; α17a; α1b; α17b; α17c; α14a; α17d; α7a; α21a; α7c; α7a; α21b; and α6.

The sequences of all of these interferon species are available on a variety of commercially available databases, including Genbank database, as well as by reference to the art (see, for example, Goeddel et al (1981) *Nature* 290:20–26; Nagata et al. (1980) *Nature* 284:3126–32; Bowden et al (1984) *Gene* 27:87–99; and Ohara and Teraoka (1987) *FEBS Letters* 211(1):78–82.

Products containing recombinant interferons are commercially available. For example, IFN-α2b is also available from U.S. Biologics; and is also the recombinant human alpha interferon protein species in the commercially available products, INTRON® A (Schering Plough); and ROFERON® A (Hoffman-La Roche).

The alpha interferon is combined with a cosmetically acceptable vehicle at a concentration of at least about 0.5 U/Ml., and not more than about 500 U/Ml., usually at a concentration of from about 1 U/mi. to not more than about 50 U/mi., and preferably at about at a concentration of from about 2.5 U/ml. to not more than about 10 U/Ml., where the units are based on a standard viral resistance assay as known in the art, e.g. bovine MBDK cells with vesicular stomatitis virus. For example, the IFN-α2b recited in the examples is based on an activity of $10^6$ units in 3 $\mu$g of recombinant protein.

The alpha interferon in the composition is preferably unencapsulated, ie. is free of liposomal encapsulation. The alpha interferon is preferably free of covalently attached fatty acids, which not present in native forms of the protein.

Optional Skin Benefit Materials and Cosmetic Adjuncts

The compositions of the invention may optionally comprise other skin benefit materials. These include estradiol; progesterone; pregnanalone; coenzyme Q10; methylsolanomethane (MSM); copper peptide (copper extract); plankton extract (phytosome); transforming growth factor beta 1 (TGF-β1); glycolic acid; kojic acid; ascorbyl palmitate; all-trans-retinol; azaleic acid; salicylic acid; broparoestrol; estrone; adrostenedione; androstanediols; etc. The steroids will generally present at a concentration of less than about 2% of the total by weight of the composition, while the other skin benefit materials may be present at higher levels, for example as much as 10 to 15%.

The compositions may further comprise sunscreens to lower skin's exposure to harmful UV rays. Sunscreens include those materials commonly employed to block ultraviolet light Illustrative compounds are the derivatives of PABA, cinnamate and derivatives of salicylate (other than ferulyl salicylate). For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. Dermascreen may also be used. The exact amount of sunscreen employed in the compositions can vary depending upon the degree of protection desired from the sun's UV radiation.

Cosmetically Acceptable Vehicle

The compositions of the invention comprise a cosmetically acceptable vehicle to act as a dilutant, dispersant or carrier for alpha interferon, so as to facilitate its distribution when the composition is applied to the skin. Vehicles other than or in addition to water can include liquid or solid emollients, solvents, humectants, thickeners and powders.

The cosmetically acceptable vehicle will usually form from 5% to 99.9%, preferably from 25% to 80% by weight of the composition, and can, in the absence of other cosmetic adjuncts, form the balance of the composition.

The compositions may be in the form of aqueous, aqueous/alcoholic or oily solutions; dispersions of the lotion or serum type; anhydrous or lipophilic gels; emulsions of liquid or semi-liquid consistency, which are obtained by dispersion of a fatty phase in an aqueous phase (O/W) or conversely (W/O); or suspensions or emulsions of smooth, semi-solid or solid consistency of the cream or gel type. These compositions are formulated according to the usual techniques as are well known to this art.

When the compositions of the invention are formulated as an emulsion, the proportion of the fatty phase may range from 5% to 80% by weight, and preferably from 5% to 50% by weight, relative to the total weight of the composition. Oils, emulsifiers and co-emulsifiers incorporated in the composition in emulsion form are selected from among those used conventionally in the cosmetic or dermatological field. The emulsifer and coemulsifier may be present in the composition at a proportion ranging from 0.3% to 30% by weight, and preferably from 0.5% to 20% by weight, relative to the total weight of the composition.

When the compositions of the invention are formulated as an oily solution or gel, the fatty phase may constitute more than 90% of the total weight of the composition.

The compositions of the invention may also contain additives and adjuvants which are conventional in the cosmetic, pharmaceutical or dermatological field, such as hydrophilic or lipophilic gelling agents, hydrophilic or lipophilic active agents, preservatives, antioxidants, solvents, fragrances, fillers, bactericides, odor absorbers and dyestuffs or colorants. The amounts of these various additives and adjuvants are those conventionally used in the field, and, for example, range from 0.01% to 10% of the total weight of the composition. Depending on their nature, these additives and adjuvants may be introduced into the fatty phase, into the aqueous phase.

Exemplary oils which may be used according to this invention include mineral oils (liquid petrolatum), plant oils (liquid fraction of karite butter, sunflower oil), animal oils (perhydrosqualen(e), synthetic oils (purcellin oil), silicone oils (cyclomethicone) and fluoro oils (perfluoropolyethers). Fatty alcohols, fatty acids (stearic acid) and waxes (paraffin wax, carnauba wax and beeswax) may also be used as fats.

Emulsifiers which may be used include glyceryl stearate, polysorbate 60, PEG-6/PEG-32/glycol stearate mixture, etc. Solvents which may be used include the lower alcohols, in particular ethanol and isopropanol, and propylene glycol.

Hydrophilic gelling agents include carboxyvinyl polymers (carbomer), acrylic copolymers such as acrylatelalkylacrylate copolymers, polyacrylamides, polysaccharides, such as hydroxypropylcellulose, natural gums and clays, and, as lipophilic gelling agents, representative are the modified clays such as bentones, fatty acid metal salts such as aluminum stearates and hydrophobic silica, or ethylcellulose and polyethylene.

An oil or oily material may be present, together with an emollient to provide either a water-in- oil emulsion or an oil-in-water emulsion, depending largely on the average hydrophilic-lipophilic balance (HLB) of the emollient employed. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

Product Use, Form, and Packaging

In use, a small quantity of the composition, for example from 1 to 100 ml, is applied to exposed areas of the skin, from a suitable container or applicator and, if necessary, it is then spread over and/or rubbed into the skin using the hand or fingers or a suitable device. The product may be specifically formulated for use as a hand, or as a facial treatment.

The cosmetic skin conditioning composition of the invention can be formulated as a lotion, a cream or a gel. The composition can be packaged in a suitable container to suit its viscosity and intended use by the consumer. For example, a lotion or cream can be packaged in a bottle, or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The following examples are put forth so as to provide those of ordinary skill in the art with a complete disclosure and description of how to make and use the subject invention, and are not intended to limit the scope of what is regarded as the invention. Efforts have been made to insure accuracy with respect to the numbers used (e.g. amounts, temperature, concentrations, etc.) but some experimental errors and deviations should be allowed for. Unless otherwise indicated, parts are parts by weight, molecular weight is weight average molecular weight, temperature is in degrees centigrade, and pressure is at or near atmospheric.

EXAMPLE 1

Example 1 illustrates topical compositions according to the present invention. The compositions can be processed in conventional manner. They are suitable for cosmetic use. In particular the compositions are suitable for application to wrinkled, rough, flaky, aged and/or UV-damaged skin and/or dry skin and post-menopausal skin to improve the appearance and the feel thereof as well as for application to healthy skin to prevent or retard deterioration thereof.

| Ingredient | % w/w |
|---|---|
| OIL-IN-WATER EMULSION | |
| DI Water | 75.40 |
| Carbomer | 0.30 |
| Disodium | EDTA 0.10 |
| Glycerin | 3.00 |
| Polysorbate | 20 2.50 |
| Butylene Glycol | 2.00 |
| Methylparaben | 0.30 |
| Triethanolamine 99% | 0.30 |
| Isopropyl Myristate | 5.00 |
| Octyl Palmitate | 3.00 |
| Cetyl Alcohol | 1.00 |
| Dimethicone 100 cst | 0.50 |
| Beeswax | 0.30 |
| Propylparaben | 0.10 |
| Germall II | 0.10 |
| Fragrance | 0.10 |
| alpha interferon, 300 U | |
| Total | 100.00 |
| OIL-IN-WATER EMULSION | |
| DI Water | 73.20 |
| Xanthan Gum | 0.20 |
| Disodium EDTA | 0.10 |
| Glycerin | 5.00 |
| Butylene Glycol | 2.00 |
| Methylparaben | 0.30 |
| Isopropyl Myristate | 5.00 |
| Octyl Palmitate | 3.00 |
| Cetyl Alcohol | 1.00 |
| Dimethicone 100 cst | 0.50 |
| Steareth-2 | 0.40 |
| Steareth-21 | 3.00 |
| Propylparaben | 0.10 |
| Germall II | 0.10 |
| Fragrance | 0.10 |
| alpha interferon, 300 U | |
| Total | 100.00 |
| WATER-IN-OIL EMULSION | |
| DI Water | 65.30 |
| Disodium EDTA | 0.10 |
| Glycerin | 3.00 |
| Propylene Glycol | 2.00 |
| Sodium Chloride | 0.70 |
| Methylparaben | 0.30 |
| Cyclomethicone | 14.00 |
| Isopropyl Myristate | 5.00 |
| Octyl Palmitate | 3.00 |
| Dimethicone Copolyol | 2.50 |
| Dimethicone 100 cst | 0.50 |
| Beeswax | 0.30 |
| Propylparaben | 0.10 |
| Germall II | 0.10 |
| Fragrance | 0.10 |
| alpha interferon, 300 U | |
| Total | 100.00 |
| HYDRO-GEL | |
| DI Water | 82.85 |
| Butylene Glycol | 5.00 |
| PPG-5-Ceteth 20 | 5.00 |
| Glycerin | 3.00 |
| Carbomer | 1.20 |
| Triethanolamine 99% | 1.20 |
| Methylparaben | 0.30 |
| Polysorbate 20 | 0.25 |
| Disodium EDTA | 0.10 |
| Germall II | 0.10 |
| alpha interferon, 300 U | |
| Total | 100.00 |
| ANHYDROUS SERUM | |
| Cyclomethicone | 72.40 |
| Isopropyl Myristate | 5.00 |
| Octyl Palmitate | 3.00 |
| Polyglycerol-6 Dioleate | 5.00 |
| Butylene Glycol | 4.00 |
| Dimethicone, 100 cst | 5.00 |
| Beeswax | 0.30 |
| Propylparaben | 0.20 |
| Fragrance | 0.10 |
| alpha interferon, 300 U | |
| Total | 100.00 |
| HYDRO-ALCOHOLIC GEL | |
| DI Water | 52.85 |
| Alcohol SDA40B | 30.00 |
| Butylene Glycol | 5.00 |
| PPG-5-Ceteth 20 | 5.00 |
| Glycerin | 3.00 |
| Carbomer | 1.20 |
| Triethanolamine 99% | 1.20 |
| 4-chromanone | 1.00 |
| Methylparaben | 0.30 |
| Polysorbate 20 | 0.25 |
| Disodium EDTA | 0.10 |
| Germall II | 0.10 |
| alpha interferon, 300 U | |
| Total | 100.00 |

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A cosmetic composition for topical treatment of skin, comprising from 0.5 to 10 U/ml of human alpha interferon 2; and a cosmetically acceptable vehicle.

2. The composition according to claim 1, wherein said alpha interferon is free of covalently bonded fatty acids or liposomes.

3. The composition according to claim 2, and further comprising one or more of estradiol; progesterone; pregnenolone; coenzyme Q10; methylsulfonylmethane (MSM); copper peptide (copper extract); plankton extract (phytosome); transforming growth factor beta-1 (TGF-$\beta$1); glycolic acid; kojic acid; ascorbyl palmitate; all trans retinol; azaleic acid; salicylic acid; broparoestrol; estrone; adrostenedione; and androstanediol.

4. The composition according to claim 2, wherein said composition further comprises a sunblock.

5. The composition according to claim 2, wherein said cosmetically acceptable vehicle is an oil in water, or water in oil emulsion.

6. A method for improving the appearance of aged, photoaged, dry, lined or wrinkled skin, the method comprising:

applying topically a cosmetic composition comprising from 0.5 to 10 U/ml of human alpha interferon 2; and a cosmetically acceptable vehicle.

7. The method according to claim 6, wherein said alpha interferon is free of covalently bounded fatty acids or liposomes.

8. The method according to claim 6, wherein said composition further comprises one or more of estradiol; progesterone; pregnenolone; coenzyme Q10; methylsulfonylmethane (MSM); copper peptide (copper extract); plankton extract (phytosome); transforming growth factor beta-1 (TGF-$\beta$1); glycolic acid; kojic acid; ascorbyl palmitate; all trans retinol; azaleic acid; salicylic acid; broparoestrol; estrone; adrostenedione; and androstanediols.

9. The method according to claim 6, wherein said composition further comprises a sunblock.

10. The method according to claim 6, wherein said cosmetically acceptable vehicle is an oil in water, or water in oil emulsion.

* * * * *